Figure 1A:
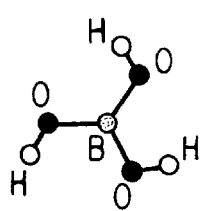

United States Patent
Kawasaki et al.

[11] Patent Number: 5,854,155
[45] Date of Patent: Dec. 29, 1998

[54] HEXAGONAL SYSTEM BORON NITRIDE POWDER

[75] Inventors: Takashi Kawasaki; Yukio Kuroda; Hiroshi Nishikawa; Hiroyuki Hara, all of Omuta, Japan

[73] Assignee: Denki Kagaku Kogyo Kabushiki Kaisha, Tokyo, Japan

[21] Appl. No.: 782,296

[22] Filed: Jan. 15, 1997

[30] Foreign Application Priority Data

Jan. 24, 1996 [JP] Japan ................................. 8-28768

[51] Int. Cl.⁶ ............................................. C04B 35/5833
[52] U.S. Cl. ...................... 501/96.4; 423/290; 524/404; 524/428
[58] Field of Search ................... 501/96.4; 423/290; 524/404, 428

[56] References Cited

U.S. PATENT DOCUMENTS

| | | | |
|---|---|---|---|
| 4,562,050 | 12/1985 | Koeda et al. | 501/96.4 |
| 4,784,978 | 11/1988 | Ogasawara et al. | 501/96.4 |
| 4,853,196 | 8/1989 | Koshida et al. | 501/96.4 |
| 4,997,633 | 3/1991 | Koshida et al. | 501/96.4 |
| 5,340,780 | 8/1994 | Sumiya | 501/96.4 |

FOREIGN PATENT DOCUMENTS

| | | |
|---|---|---|
| 0 137 652 | 4/1985 | European Pat. Off. . |
| 362007610 | 1/1987 | Japan . |
| 362059506 | 3/1987 | Japan . |
| 408290905 | 11/1996 | Japan . |
| 409202663 | 8/1997 | Japan . |

*Primary Examiner*—Karl Group
*Attorney, Agent, or Firm*—Oblon, Spivak, McClelland, Maier & Neustadt, P.C.

[57] ABSTRACT

Melamine borate particles each consisting essentially of needle crystal primary particles of melamine borate ($C_3N_6H_6 \cdot 2H_3BO_3$) which are aggregated to one another.

6 Claims, 6 Drawing Sheets

BORIC ACID

MELAMINE

MELAMINE BORATE

HEXAGONAL SYSTEM BORON NITRIDE POWDER

The present invention relates to melamine borate particles, a method for their production, hexagonal system boron nitride particles and a hexagonal system boron nitride powder produced by using such melamine borate particles, a resin/or rubber composite containing the hexagonal system boron nitride powder, a powder material for preparation of a sintered body of hexagonal system boron nitride, a hexagonal system boron nitride sintered body obtained by sintering such a powder material for preparation of a sintered body of hexagonal system boron nitride, and a method for producing a hexagonal system boron nitride powder.

Hexagonal system boron nitride (hereinafter referred to as "hBN") particles have a layer structure similar to graphite, and hBN powder as their aggregates, is excellent in such properties as thermal conductivity, insulating property, chemical stability, solid lubricant property and thermal shock resistance and is used as a solid lubricant or release agent, as a filler for a resin or rubber, or as a material for preparation of a hBN sintered body. The hBN powder is hardly sinterable. Accordingly, to prepare its sintered body, it is common to add a sintering assistant, followed by sintering by a hot pressing method or a pressureless sintering method. The hBN sintered body being one of rare machinable ceramics, is used for a crucible for sintering ceramics, a heat resistant jig, a high temperature insulating material or the like.

The following methods are available as conventional methods for producing hBN powders. However, in either method, the product will be in a scaly particle form, and if it is used by itself as a filler for a resin or rubber or as a starting material for a sintered body, the particles tend to align in a certain direction (hereinafter referred to as "orientation"), whereby anisotropy is likely to be observed in the properties of the resulting resin or rubber molded product or in the hBN sintered body.

(1) A method in which a compound containing boron and oxygen, such as boric acid, boron oxide or borax, is supported on a filler such as calcium phosphate, followed by firing in an ammonia atmosphere.

(2) A method in which a mixture comprising a boron compound and a nitrogen-containing compound such as dicyanodiamide, melamine or urea, is fired.

(3) A method in which water is removed from a mixture comprising boric acid, melamine and water, by a method such as filtration, centrifugal separation or drying, followed by firing in a non-oxidizing gas atmosphere.

To efficiently remove heat generated from an electronic part, an electrically insulating heat conductive sheet (hereinafter referred to simply as "an insulating heat radiation sheet") is used between the electronic part and a radiation fin. As such an insulating heat radiation sheet, the one having a hBN powder dispersed in silicone rubber, is used, and to further improve the heat conductivity, it is attempted to increase the filling proportion of the hBN powder. However, in such a case, there is a problem such that the flexibility is likely to be lost, or mechanical properties such as tensile strength tend to deteriorate. Accordingly, there is a limit in improving the heat conductivity by increasing the filling proportion of the hBN powder.

Further, usual hBN particles are scaly, and the heat conductivity is higher in the plane direction (a-axis direction) than in the thickness direction (c-axis direction). In an insulating heat radiation sheet having such a hBN powder incorporated, the a-axis direction of hBN particles tends to align perpendicularly to the thickness direction of the insulating heat radiation sheet, whereby the heat conductivity used to be poor in the thickness direction as compared with the plane direction of the insulating heat radiation sheet.

To solve such a problem, an attempt has been made to employ a hBN powder having a shape other than a scaly shape. Such a hBN powder is, for example, hBN blocks wherein crystals are undeveloped, a hBN powder granulated by e.g. spray drying, or a hBN powder prepared by pulverizing a sintered body of hBN.

However, the hBN blocks wherein crystals are undeveloped, are inferior to the scaly hBN powder in such properties as purity and heat conductivity, whereby not only the heat conductivity in the thickness direction of the insulating heat radiation sheet will not be improved, but the reliability in moisture resistance tends to deteriorate. The granulated hBN powder is likely to be disintegrated when kneaded to rubber, whereupon the a-axis direction of hBN particles will align perpendicularly to the thickness direction of the insulating heat radiation sheet. In the case of the powder prepared by pulverizing the sintered body of hBN, hBN particles tend to align at the time of hot pressing or preliminary molding in the process for preparing the sintered body of hBN, and the proportion of particles having primary particles aggregated in an oriented state, tends to be large, whereby the a-axis direction of hBN particles tend to align perpendicularly to the thickness direction of the insulating heat radiation sheet, although a certain effect for improvement may be observed. Further, such a powder is costly.

Now, a hBN sintered body will be described. As a method for preparing a hBN sintered body, a method of hot pressing a hBN powder which has low crystallinity and contains a substantial amount of $B_2O_3$ is available (JP-B-49-37093). However, by this method, $B_2O_3$ will remain in the hBN sintered body, and to remove it, heat treatment under a reduced pressure atmosphere is further required, which adds to the cost. As a sintering method which requires no treatment for purification, an atmospheric pressure sintering method has been proposed (JP-A-3-115109, JP-A-6-48839), but by such a method, hBN undergoes volume expansion during the sintering, whereby the density of the sintered body tends to be low.

Therefore, in order to produce a hBN sintered body having a high purity and high density, a method has been proposed in which high filling hBN powder is used for pressureless sintering (JP-A-7-315937). However, the hBN powder used in this method is a scaly coarse powder having a large particle size, as disclosed in JP-B-62-27002 or JP-A-7-41311. Accordingly, hBN particles are likely to be oriented at the time of hot pressing or preliminary molding, whereby a substantial anisotropy will result in the strength of the hBN sintered body. Therefore, when finishing the surface in a direction parallel to the direction in which the strength in the machining is weak (the c-axis direction of hBN particles), a problem of chipping is likely to result. Further, a hBN powder granulated by spray drying is not suitable as a starting material for preparation of a hBN sintered body, since it has a low density.

In a case where it is desired to improve the strength even at a sacrifice of the excellent properties of hBN to some extent, a method may be employed in which a sintering assistant is added to a hBN powder, followed by hot pressing (JP-B-49-40124). However, by the hot pressing method, the shape of the product is restricted, and the processing loss tends to be substantial. Further, the processing costs will be high, as the product is a sintered body having high strength.

By the pressureless sintering method for hBN employing a sintering assistant (JP-A-1-131065), it is possible to produce a large size product or a product of a complicated shape, but the density of the sintered body tends to be low. To overcome such a difficulty, it has be proposed to carry out sintering in a deoxidating atmosphere (JP-B-5-32349, JP-B-7-53614), but control of the atmosphere is cumbersome.

Under these circumstances, for the hBN sintered body, it is desired to develop a technique for producing a hBN sintered body which has a high density and high strength and has a shape close to the shape of final product.

It is an object of the present invention to provide a resin or rubber molded product having less anisotropy.

Another object of the present invention is to provide a hBN sintered body having high purity, high density and high strength.

A further object of the present invention is to provide a hBN sintered body which has high density, high strength and less anisotropy and which has a shape close to the shape of the final product.

Such objects of the present invention can be accomplished by producing novel melamine borate ($C_3N_6H_6 \cdot 2H_3BO_3$) particles formed by maintaining a mixture of boric acid and melamine in an atmosphere containing steam, or a mixture containing such particles, and crystallizing such particles or mixture to produce hBN particles each consisting of scaly primary particles which are aggregated, or a hBN-powder containing such hBN particles.

Namely, the present invention provides:
1. Melamine borate particles each consisting essentially of needle crystal primary particles of melamine borate ($C_3N_6H_6 \cdot 2H_3BO_3$) which are aggregated to one another.
2. A method for producing melamine borate particles, which comprises maintaining a mixture of boric acid and melamine at a temperature (T) of from 0° to 200° C., in an atmosphere containing steam so that the relative humidity ($\psi$) is at least 5%, for a retention time (t) within a range of from 1 to 100 hours, and under a condition that satisfies a formula $(T-60) \geq -20 \cdot \log_{10}(t/4) + (\psi-100)^2/20$, to form melamine borate particles as defined in above item 1 or a mixture containing them.
3. Hexagonal system boron nitride particles each consisting essentially of scaly primary particles of hexagonal system boron nitride which are aggregated to one another without orientation.
4. The hexagonal system boron nitride particles according to above item 3, wherein the primary particles are aggregated to one another in a pinecone form without a binder.
5. A hexagonal system boron nitride powder, which is a mixture comprising from 20 to 100 wt % of hexagonal system boron nitride particles as defined in above item 3 or 4 and from 80 to 0 wt % of other boron nitride particles, and which has a graphitization index (GI) of from 1.0 to 2.5 by powder X-ray diffractometry and a ratio of $I_{002}/I_{100}$ of from 6 to 20, where $I_{002}$ is the intensity of the (002) diffraction line and $I_{100}$ is the intensity of the (100) diffraction line
6. A method for producing a hexagonal system boron nitride powder as defined in above item 5, which comprises mixing melamine borate particles or a mixture containing them, produced by the method as defined in claim 2, and a crystallization catalyst, so that the molar ratio of the melamine borate to the crystallization catalyst, as calculated as $B_2O_3$, i.e. $C_3N_6H_6 \cdot 2H_3BO_3/B_2O_3$, is from 5 to 100, and firing the resulting mixture in a non-oxidizing gas atmosphere at a temperature of from 1,700° to 2,200° C.
7. A method for producing a hexagonal system boron nitride powder as defined in above item 5, which comprises calcining melamine borate particles or a mixture containing them, produced by the method as defined in claim 2, in a non-oxidizing gas atmosphere at a temperature of not lower than 500° C. and lower than 1,700° C., to form amorphous boron nitride or hexagonal system boron nitride having a graphitization index (GI) exceeding 2.5, then mixing thereto a crystallization catalyst so that the molar ratio of nitrogen (N) of the boron nitride to the crystallization catalyst, as calculated as $B_2O_3$, i.e. $N/B_2O_3$, is from 10 to 300, and firing the resulting mixture in a non-oxidizing gas atmosphere at a temperature of from 1,700° to 2,200° C.
8. A composite comprising a resin and/or rubber, and a hexagonal system boron nitride powder as defined in above item 5, incorporated thereto.
9. A powder material for preparation of a sintered body of hexagonal system boron nitride, which contains a hexagonal system boron nitride powder as defined in above item 5 and has an oxygen content of from 0.5 to 2.5 wt %.
10. A hexagonal system boron nitride powder material for preparation of a pressureless sintered body, which comprises a hexagonal system boron nitride powder as defined in above item 5, and at least one member selected from the group consisting of boron oxides, alkaline earth metal oxides and alkaline earth metal borates, incorporated to the powder in an amount of from 1 to 20 wt %.
11. A sintered body of hexagonal system boron nitride obtained by sintering a hexagonal system boron nitride powder as defined in above item 9.
12. A pressureless sintered body of hexagonal system boron nitride obtained by pressureless sintering of a hexagonal system boron nitride powder as defined in above item 10.

Figure 1B:
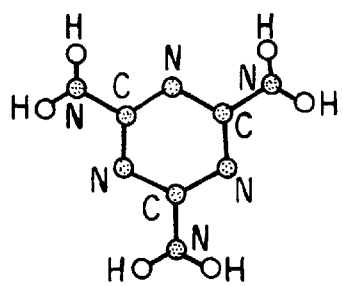
Figure 1C:
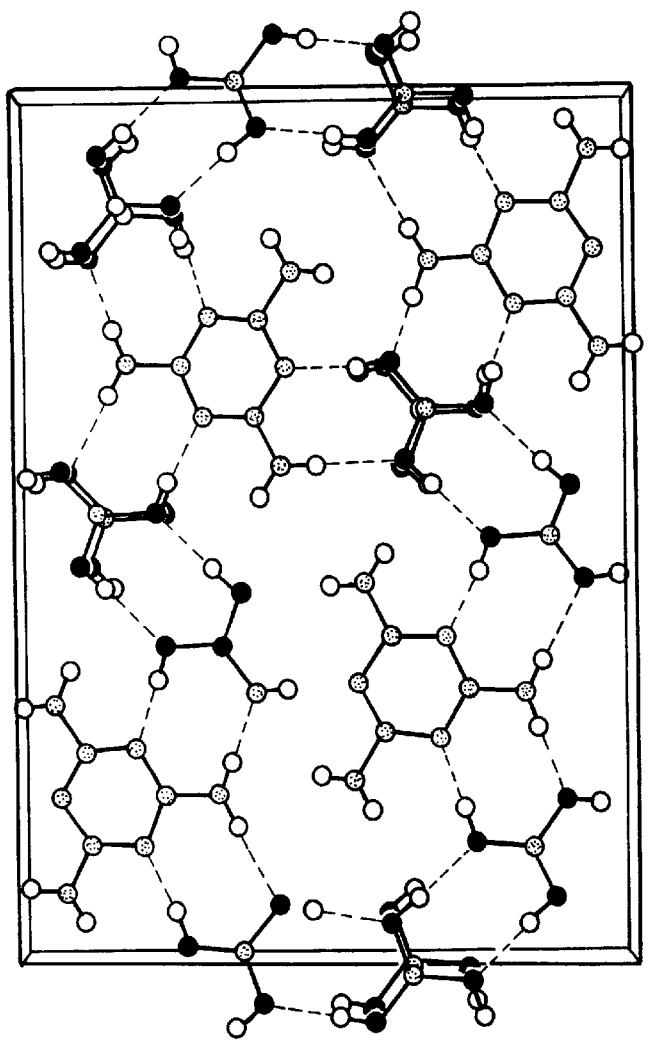
Figure 2:
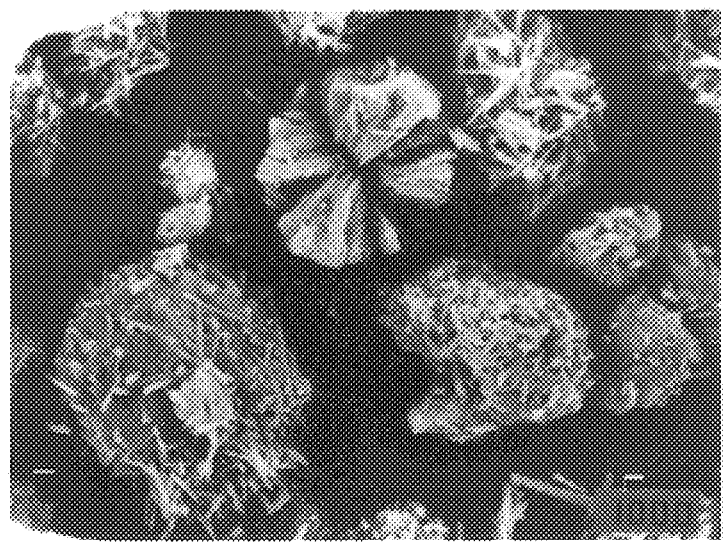
Figure 4:
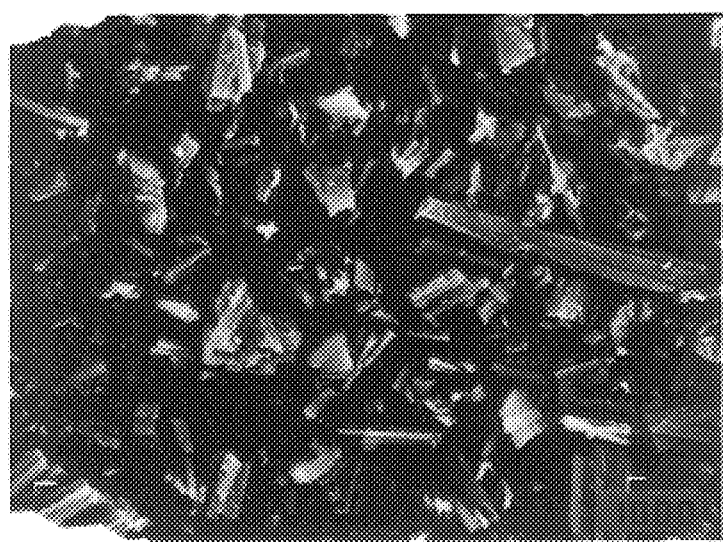
Figure 3:
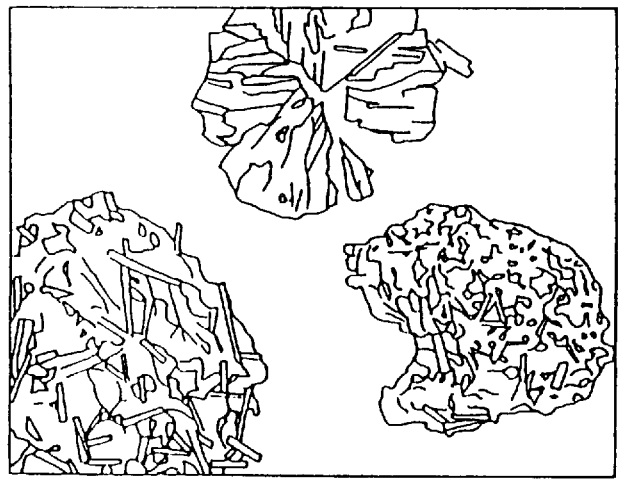
Figure 5:
Figure 6:
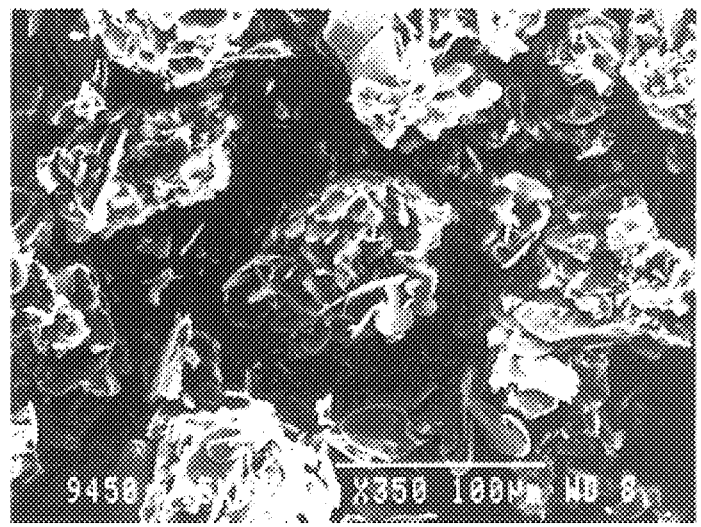
Figure 7:
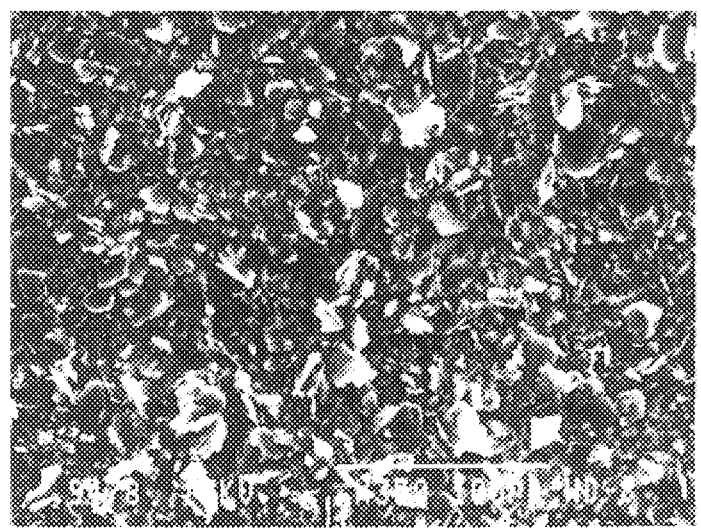
Figure 8:
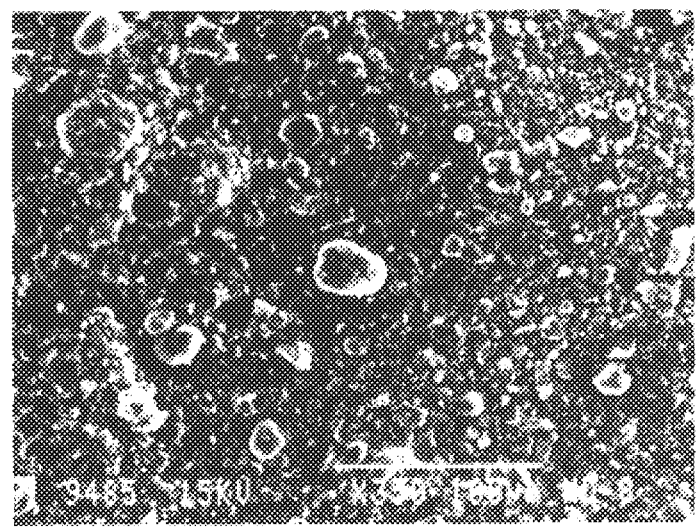
Figure 9:
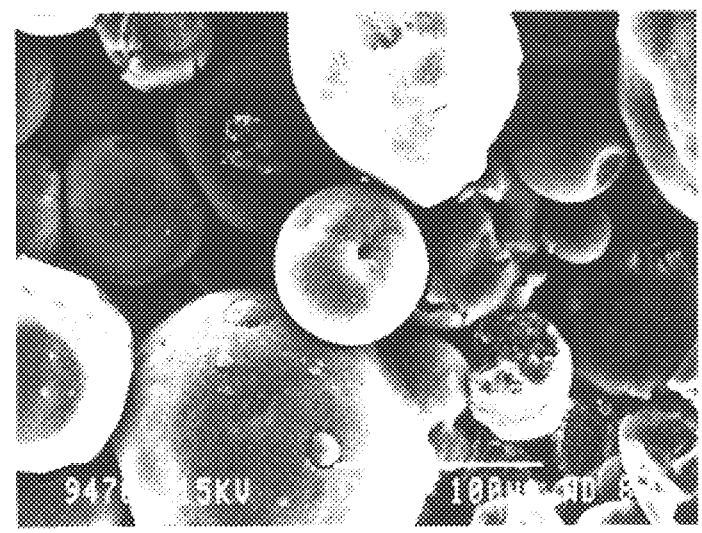
Figure 10:

In the accompanying drawings:
FIG. 1(a) shows the molecular structure of boric acid.
FIG. 1(b) shows the molecular structure of melamine.
FIG. 1(c) shows the crystal structure of melamine borate.
FIG. 2 is a SEM photograph with 1,000 magnifications of a mixture containing melamine borate particles.
FIG. 3 is a simulation of FIG. 2.
FIG. 4 is a SEM photograph with 1,000 magnifications of a mixture containing conventional melamine borate particles composed of needle crystals.
FIG. 5 is a simulation of FIG. 4.
FIG. 6 is a SEM photograph with 350 magnifications of a hBN powder containing hBN particles of the present invention.
FIG. 7 is a SEM photograph with 350 magnifications of a hBN powder containing conventional hBN particles wherein primary particles are not aggregated.
FIG. 8 is a SEM photograph with 350 magnifications of a hBN powder containing conventional hBN blocks wherein crystals are undeveloped.
FIG. 9 is a SEM photograph with 350 magnifications of a hBN powder containing conventional granulated hBN particles.
FIG. 10 is a SEM photograph with 350 magnifications of a hBN powder containing conventional hBN particles obtained by pulverizing a hBN sintered body.

Now, the present invention will be described in detail with reference to the preferred embodiments.

FIG. 1(c) shows the crystal structure of melamine borate particles of the present invention. FIG. 2 shows a secondary electron image (SEM photograph) of a mixture containing such particles, and FIG. 3 shows a simulation of FIG. 2. Further, FIG. 4 shows a SEM photograph of a mixture containing conventional melamine borate particles, and FIG. 5 shows a simulation of FIG. 4. Further, the molecular structures of boric acid and melamine are shown in FIG. 1(a) and FIG. 1(b), respectively.

As is evident from a comparison of the above drawings, the melamine borate particles of the present invention are different from the conventional melamine borate particles in that needle crystal primary particles of melamine borate are aggregated to one another, although the crystal structure of the melamine borate is not different as compared with the conventional melamine borate particles.

The process for producing melamine borate particles of the present invention will be described hereinafter.

Now, the hBN particles of the present invention will be described. Referring to FIG. 6 showing a SEM photograph of a hBN powder containing the hBN particles, the hBN particles of the present invention are characterized in that the primary particles, preferably scaly primary particles, of hBN are aggregated to one another without orientation, for example, in a pinecone form, without a binder. Here, the term "aggregated" is distinguished from "agglomerated" by granulation and indicates a state where a weak chemical bond (such as cohesion or adhesion) is partially present among the primary particles, whereby the aggregated particles will not be disintegrated when they are kneaded with resin and/or rubber.

Conventional hBN particles are non-aggregated scaly particles (FIG. 7 shows a SEM photograph of a hBN powder containing such hBN particles), hBN blocks wherein crystals are undeveloped (FIG. 8 shows a SEM photograph of a hBN powder containing such hBN particles), granulated particles (FIG. 9 shows a SEM photograph of a hBN powder containing such hBN particles) or particles obtained by pulverizing a hBN sintered body (FIG. 10 shows a SEM photograph of a hBN powder containing such hBN particles). These conventional particles and the hBN particles of the present invention are different in the following respects.

(i) In the non-aggregated scaly particles, primary particles are discrete and not aggregated.

(ii) The hBN blocks wherein crystals are undeveloped, have lower crystallinity than the hBN particles of the present invention.

(iii) In the granulated hBN particles, scaly primary particles are not aggregated.

(iv) The hBN particles obtained by pulverizing a hBN sintered body are aggregates of scaly primary particles, but the primary particles are aggregated with orientation or by means of a binder in the case of aggregates wherein primary particles are not oriented.

Accordingly, when hBN powders containing such conventional particles, are used to prepare resin and/or rubber shaped products or hBN sintered bodies, there will be the following problems.

Namely, the hBN powder containing the non-aggregated scaly particles, is likely to orient in the resin and/or rubber molded product. The hBN powder containing hBN blocks wherein crystals are undeveloped, is inferior in the purity or heat conductivity, whereby the properties of the resin and/or rubber molded product tend to be inferior. With the hBN powder containing granulated hBN particles, the granulated particles will be disintegrated during kneading with a resin and/or rubber and will then be oriented. Further, it is a low density powder, whereby the density of a hBN sintered body obtainable by sintering it, will also be low. With the hBN powder containing particles obtained by pulverizing a hBN sintered body, hBN particles themselves are aggregated in an oriented state, and accordingly they will remain oriented also in the resin and/or rubber molded product. Further, the heat conductivity tends to be low, since a binder is used.

Whereas, with the hBN powder of the present invention, even when it is kneaded into a resin and/or rubber, the primary particles of hBN will maintain the agglomerated state without being oriented, whereby no anisotropy will be formed in the properties of the resin and/or rubber molded product, or even when formed, such anisotropy will be very small. Further, in the hBN particles of the present invention, the primary particles are aggregated to one another without any binder, whereby high heat conductivity inherent to hBN can be obtained, and the particle form is stable, for example, even when acid treatment for purification is applied thereto.

The hBN powder of the present invention is a mixture which preferably comprises from 20 to 100 wt % of the hBN particles of the present invention and from 80 to 0 wt % of hBN particles other than the hBN particles of the present invention.

The hBN particles other than the hBN particles of the present invention may, for example, be conventional non-aggregated scaly particles, hBN blocks wherein crystals are undeveloped, granulated particles or particles obtained by pulverizing a hBN sintered body.

With the hBN powder of the present invention, it is desired that its crystallinity is high, and the graphitization index (GI) by powder X-ray diffractometry is preferably from 1 to 2.5, more preferably from 1.4 to 1.6. GI can be obtained by calculating the integrated intensity ratio i.e. the area ratio of (100), (101) and (102) diffraction lines in the X-ray diffraction pattern (J. Thomas, et. al, J. Am. Chem. Soc. 84, 4619 (1962)).

$$GI=[area\{(100)+(101)\}]/[area(102)]$$

Further, with the hBN powder of the present invention, it is desired that its orientation is low, and the ratio of $I_{002}/I_{100}$ (hereinafter referred to as "OI" i.e. an abbreviation of Orientation Index) is preferably from 6 to 20, where $I_{002}$ is the intensity of the (002) diffraction line and $I_{100}$ is the intensity of the (100) diffraction line by the powder X-ray diffractometry. This OI value is characterized in that it is smaller than OI of conventional highly crystalline hBN powders which used to exceed 20.

Further, with the hBN powder of the present invention, it is desired that its BN purity is at least 90 wt %.

Now, the process for producing the hBN powder of the present invention will be described.

A feature of the process for producing the hBN powder of the present invention is that melamine borate ($C_3N_6H_6 \cdot 2H_3BO_3$) particles having a novel structure, formed by maintaining a mixture of boric acid and melamine in an atmosphere containing a proper amount of steam, or a mixture containing such particles, is used as the starting material. The melamine borate particles to be used in the present invention, have a crystal structure having two molecules of boric acid hydrogen-bonded to one molecule of melamine, as shown in FIG. 1(c), and are the ones wherein needle crystal primary particles are aggregated (see FIGS. 2 and 3). Conventional melamine borate particles or a mixture containing them, is formed by mixing boric acid, melamine and water, and it is used as a starting material for producing a hBN powder (U.S. Pat. No. 3,241,918, JP-A-60-151202, JP-A-61-191505, JP-A-61-286207, etc.). However, in this method, liquid water is employed, whereby needle crystals of melamine borate are not aggregated (see FIGS. 4 and 5). Accordingly, the hBN powder produced by using such a starting material will be scaly particles, where scaly primary particles are not aggregated (see FIG. 7).

The boric acid to be used in the present invention is the one which reacts with melamine to form melamine borate, and it may, for example, be one or more compounds represented by the formula $(B_2O_3) \cdot (H_2O)_x$, wherein x is from 0 to 3, such as orthoboric acid ($H_3BO_3$), metaboric acid ($HBO_2$), tetraboric acid ($H_2B_4O_7$) and boric anhydride ($B_2O_3$). Among them, orthoboric acid is particularly suitable for the present invention, since it is readily available and can easily be mixed with melamine. The boric acid and the melamine are preferably as pure as possible.

The boric acid and the melamine may be mixed by means of a usual mixing machine such as a ball mill, a ribbon blender or a Henschel mixer. The blend proportions are preferably such that the atomic ratio of B/N is from 1/1 to 1/6, particularly from 1/2 to 1/4, where B is boron atoms in the boric acid and N is nitrogen atoms in the melamine. If the ratio of B/N exceeds 1/1, the residual amount of unreacted boric acid tends to be remarkable, and such boric acid acts as an excessive crystallization catalyst, whereby the resulting hBN powder tends to be scaly particles, which are scarcely aggregated. Further, if the atomic ratio of B/N is less than 1/6, sublimation of unreacted melamine during firing tends to be remarkable, whereby the yield decreases.

With respect to the conditions for maintaining the mixture of boric acid and melamine in an atmosphere containing steam, the atmosphere is the one containing steam at a relative humidity of at least 5% at a temperature of from 0° to 200° C., preferably from 40° to 100° C. If the temperature is lower than 0° C., the reaction rate will be very low, and the resulting needle crystals of melamine borate tend to be hardly aggregated. On the other hand, if the temperature exceeds 200° C., boric acid will melt in a vitreous state, whereby the surface area decreases, and the conversion will not increase. Further, the relative humidity of the atmosphere for forming melamine borate is set to be at least 5% for such a reason that in an atmosphere with a relative humidity of less than 5%, the reaction rate will be very low, and the resulting needle crystals of melamine borate tend to be hardly aggregated. The retention time is usually from 1 to 100 hours.

Even under the above conditions, most preferred is a condition such that the temperature T (°C.), the relative humidity $\psi$ (%) and the retention time (t) satisfy the formula of $(T-60) \geq -20 \cdot \log_{10}(t/4)+(\psi-100)^2/20$. Such an atmosphere can easily be formed by using a thermostatic humidistat, a steam oven. With respect to an atmospheric gas other than steam, there is no particular restriction, and the air, a nitrogen gas or an inert gas may, for example, be used.

In the present invention, melamine borate particles of the present invention can be obtained by separating melamine borate particles from the melamine borate particles produced as described above or from a mixture containing them.

In the process for producing the hBN powder of the present invention, the melamine borate particles prepared as described above or a mixture containing them, is crystallized by means of a conventional crystallization catalyst. The crystallization catalyst to be used in the present invention is preferably the one which is inexpensive and the catalytic ability of which is scarcely varied in the firing process. Such a catalyst may, for example, be boric acid, a borate of an alkali metal or alkaline earth metal, or an alkali metal or alkaline earth metal compound which is capable of forming a borate of an alkali metal or alkaline earth metal by a reaction with boric acid. More specifically, the borate of an alkali metal or alkaline earth metal may, for example, be anhydrous borax ($Na_2B_4O_7$) or calcium borate ($\chi CaO \cdot B_2O_3$, wherein $\chi$ is from 0.5 to 3), and the alkali metal or alkaline earth metal compound capable of forming a borate an alkali metal or alkaline earth metal by a reaction with boric acid, may, for example, be sodium carbonate ($Na_2CO_3$) or calcium carbonate ($CaCO_3$).

The timing for addition of the crystallization catalyst may be at the time of mixing the starting materials, at the stage when melamine borate has been formed, or at the stage after forming amorphous BN or hBN having low crystallinity with GI exceeding 2.5 in a case where calcination is carried out. When calcination is carried out, it may be added both before and after the calcination.

When added at the time of mixing the starting materials, the crystallization catalyst is used in such an amount that the molar ratio ($C_3N_6H_6 \cdot 2H_3BO_3/B_2O_3$) of the melamine borate ($C_3N_6H_6 \cdot 2H_3BO_3$) to the crystallinity catalyst, as calculated as $B_2O_3$, will be from 5 to 100. When added after calcination of the starting material to obtain amorphous BN or hBN having low crystallinity with GI exceeding 2.5, the crystallization catalyst is used in such an amount that the molar ratio ($N/B_2O_3$) of the nitrogen (N) of the hBN to the crystallization catalyst, as calculated as $B_2O_3$, will be from 10 to 300. If the molar ratio is larger than the above range (i.e. the amount of the catalyst is smaller), the resulting hBN powder tends to have low crystallinity, and if it is smaller (i.e. the amount of the catalyst is larger), the resulting hBN powder tends to be scaly particles which are hardly aggregated.

The firing is carried out in such a manner that the melamine borate particles or a mixture containing them and the crystallization catalyst are mixed, and the mixture is fired in a non-oxidizing gas atmosphere at a temperature of from 1,700° to 2,200° C., or in such a manner that the melamine borate particles or a mixture containing them is preliminarily calcined in a non-oxidizing gas atmosphere at a temperature of at least 500° C. and lower than 1,700° C. to obtain amorphous BN or hBN with GI exceeding 2.5, then the crystallization catalyst is added thereto, and the mixture is fired in a non-oxidizing gas atmosphere at a temperature of from 1,700° to 2,200° C. If the firing temperature is lower than 1,700° C., the hBN powder tends to have low crystallinity, and if it exceeds 2,200° C., decomposition of the hBN powder tends to be remarkable. The non-oxidizing gas may, for example, be nitrogen gas, hydrogen gas, ammonia gas, a hydrocarbon gas such as methane or propane, a rare gas such as helium or argon, or carbon monoxide gas. Among these, nitrogen gas is most suitable, since it is readily available and inexpensive, and yet it has a large effect for suppressing decomposition of hBN at a high temperature of from 2,000° to 2,200° C. The time for the firing is preferably from 0.5 to 24 hours, more preferably from 2 to 10 hours.

The firing furnace may, for example, be a batch system furnace such as a muffle furnace, a tubular furnace or an atmospheric gas furnace, or a continuous system furnace such as a rotary kiln, a screw conveyor furnace, a tunnel furnace, a belt furnace, a pushing furnace or a vertical continuous furnace. These furnaces may be selected for use depending upon the particular purposes. For example, when various types of hBN powders are produced in small amounts, a batch system furnace may be employed, and when a certain predetermined type of the product is produced in a large amount, a continuous system furnace may be employed.

In the hBN powder of the present invention, the proportions of the hBN particles of the present invention and other hBN particles, can be adjusted by e.g. the amount of the crystallization catalyst and the firing temperature. For example, if the amount of the crystallization catalyst is increased, the proportion of non-aggregated scaly hBN particles increases, and if the firing temperature is low, the proportion of hBN blocks in which crystals are undeveloped, tends to increase.

The hBN powder of the present invention prepared as described above, may be subjected to post treatment such as pulverization, classification, removal of the remaining crystallization catalyst by acid treatment (purification), washing or drying, as the case requires, and then used for practical applications.

Now, the applications of the hBN powder of the present invention will be described.

Firstly, the resin and/or rubber composite of the present invention will be described. The content of the hBN powder of the present invention in the resin and/or rubber composite of the present invention varies depending upon the type of the resin and/or rubber and the particular use of the composite. However, it is usually from 20 to 97 vol %, preferably from 40 to 90 vol %. If the content is less than 20 vol %, the thermal shock resistance or the moisture resistance of the resin and/or rubber composite tends to be low, although the moldability will be excellent. On the other hand, if it exceeds 97 vol %, the moldability tends to be poor, and non-filled portions or voids are likely to form, whereby the electrical insulating property or reliability will be impaired.

The resin to be used in the present invention may, for example, be an epoxy resin such as a bisphenol type epoxy resin, a phenol novolak type epoxy resin, an alicyclic type epoxy resin, a heterocyclic type epoxy resin, a glycidyl ester type epoxy resin, a glycidyl amine type epoxy resin or a halogenated epoxy resin, a polybenzimidazole, a polybenzoxazole, a polybenzthiazole, a polyoxadiazole, a polypyrazole, a polyquinoxaline, a polyquinazolinedione, a polybenzoxadinone, a polyindolone, a polyquinazolone, a polyindoxyl, a silicone resin, a silicone-epoxy resin, a phenol resin, a melamine resin, a urea resin, an unsaturated polyester, a polyaminobismaleimide, a diallyl phthalate resin, a fluorine resin, a methylpentene polymer, a polyimide, a polyamideimide, a polyetherimide, a polyamide such as 66-nylon, MXD-nylon or amorphous nylon, a polyester such as polybutylene terephthalate or polyethylene phthalate, a polyphenylene sulfide, a modified polyphenylene ether, a polyallylate, a total aromatic polyester, a polysulfone, a liquid crystal polymer, a polyetheretherketone, a polyethersulfone, a polycarbonate, a maleimide-modified resin, an ABS resin, an AAS (acrylonitrile/acryl rubber/styrene) resin, or an AES (acrylonitrile-ethylene/propylene/diene rubber-styrene) resin.

The curing agent for the epoxy resin may, for example, be a phenol type curing agent such as phenol novolak or cresol novolak, or an acid anhydride type curing agent such as tetrahydrophthalic anhydride, hexahydrophthalic anhydride or methylhexahydrophthalic anhydride. It is preferably used in an amount of from 30 to 90 parts by weight per 100 parts by weight of the epoxy resin.

The rubber to be used in the present invention may, for example, be natural rubber or a synthetic rubber such as butyl rubber, acryl rubber, ethylene propylene rubber, silicone rubber, polyester elastomer or polybutadiene.

Further, the following curing accelerator, catalyst, vulcanization agent, lubricant/release agent, stabilizer, photostabilizer, coloring agent, flame regardant, coupling agent, etc., may be incorporated to the resin and/or rubber composite of the present invention, as the case requires.

The curing accelerator may, for example, be a nitrogen-containing curing accelerator, such as benzoguanamine, 2,4-dihydrazino-6-methylamino-S-triazine, an imidazole derivative such as 2-methylimidazole, 2-ethyl-4-methylimidazole or 1-cyanoethyl-2-ethyl-4-methylimidazole, various amine complexes of boron fluoride, a tertiary amine compound such as trisdimethylaminomethylphenol, 1,8-diazobicyclo(5,4,0)-undecene-7 or benzyldimethylamine, dicyandiamide, an aminoalcohol compound obtained by a reaction of a bisphenol type epoxy resin or a cresol novolak type epoxy resin with ammonia, or adipic acid hydrazide, or an organic phosphine type curing accelerator such as triphenylphosphine, tricyclohexylphosphine, methyldiphenylphosphine, tritolylphosphine, 1,2-bis(diphenylphosphino)ethane, or bis(diphenylphosphino)methane.

The catalyst may, for example, be a curing catalyst such as bis-(tributyltin)oxide, tin dioctenoate, antimony octanoate, tin butyrate, lead monoxide, lead sulfide or lead carbonate, or a polymerization catalyst such as a platinum compound.

The vulcanization agent may, for example, be benzoyl peroxide or dicumyl peroxide.

The lubricant/release agent may, for example, be carnauba wax, montan wax, polyester oligomer, silicone oil, low molecular weight polyethylene, paraffin, a metal salt of a linear fatty acid, an acid amide or an ester.

The stabilizer may, for example, be 2,6-di-t-butyl-4-methylphenol, 1,3,5-tris(2-methyl-4-hydroxy-5-t-butylphenol)butane, distearylthio dipropionate, trinonylphenyl phosphite or tridecyl phosphite.

The photostabilizer may, for example, be 2,2'-dihydroxy-4-methoxybenzophenone, 2(2'-hydroxy-5-methylphenyl)benzotriazole, 4-t-butylphenylsalicylate, or ethyl 2-cyano-3,3-diphenylacrylate.

The colorant may, for example, be iron oxide red or carbon black.

The flame retardant may, for example, be antimony trioxide, antimony tetraoxide, triphenylstilbene, hydrated alumina, ferrocene, phosphagen, hexabromobenzene, tetrabromophthalic anhydride, tricresyl phosphate, tetrabromo-bisphenol A or a brominated epoxy derivative.

The coupling agent may, for example, be a silane-type coupling agent such as vinyl trimethoxysilane, γ-glycidoxypropyl trimethoxysilane, γ-ureidopropyl triethoxysilane, N-β-(aminoethyl)-γ-aminopropyl trimethoxysilane or β-(3,4-epoxycyclohexyl)ethyl trimethoxysilane, a titanium type coupling agent such as isopropyl triinstearoyl titanate, dicumylphenyloxyacetate titanate, bis(dioctylpyrophosphate)oxyacetate titanate or isopropyltridecylbenzenesulfonyl titanate, or an aluminum type coupling agent such as acetoalkoxyaluminum diisopropylate.

Now, the hBN sintered body and the starting material powder for producing the hBN sintered body of the present invention will be described.

Firstly, the starting material powder for producing a hBN sintered body of high purity and high strength excellent in mechanical properties, is preferably the one having an oxygen content of from 0.5 to 2.5 wt %, which is prepared by mixing to the hBN powder of the present invention a hBN powder different in the oxygen content. If the oxygen content is less than 0.5 wt %, the strength of the sintered body tends to be low. The upper limit of the oxygen content is preferably 1.5 wt % in the case where sintering is carried out by hot pressing, or 2.5 wt % when sintering is carried out by a pressureless sintering method. If the oxygen content increases, the purity of the sintered body decreases.

The hBN powder different in the oxygen content, to be incorporated to the hBN powder of the present invention, is preferably the one having a specific surface area of at least 20 m$^2$/g, more preferably at least 30 m$^2$/g, as measured by a BET method and an oxygen content of from 1.5 to 4.0 wt %. The mixing may be carried out by a common method by means of a ribbon blender or a ball mill. However, it is necessary to take a due care not to destroy the form of the hBN particles of the present invention.

The method for sintering the starting material powder may be either a hot pressing method or a pressureless sintering method. In the hot pressing method, the surface pressure is preferably at least 100 kg/cm$^2$, and the sintering temperature is preferably at least 1,600° C. These conditions can be suitably adjusted depending upon the properties required for the sintered body. In the case of the pressureless sintering method, green forming is carried out by a metal mold forming, a CIP forming or a combination thereof, and then the green is sintered in an inert gas atmosphere at a temperature of at least 1,800° C. To obtain a sintered body of a high density, the green forming pressure is preferably at least 2,000 kg/cm$^2$.

The starting material powder for producing a hBN sintered body of a high density and high strength with a small anisotropy, is the one having one or more members selected from the group consisting of boron oxide and oxides and borides of alkaline earth metals, incorporated to the hBN powder of the present invention in an amount of from 1 to 20 wt %, preferably from 3 to 15 wt %. If the amount is less than 1 wt %, the strength of the sintered body tends to be low, and if it exceeds 20 wt %, the purity tends to decrease. Such an additive may be mixed by a common method, but in order to uniformly disperse it, it is preferred that the additive is preliminarily finely pulverized.

For the above additive, it is preferred to use boron oxide and an alkaline earth metal oxide in combination or a borate of an alkaline earth metal. The proportion of such an additive is preferably such that the molar ratio of the alkaline earth metal/B$_2$O$_3$ is from 1/10 to 2.5/1. If the molar ratio is less than 1/10, the strength of the sintered body tends to be low, and if it exceeds 2.5/1, the color of the sintered body will change from white.

With respect to the sintering method of such a starting material powder, the pressureless sintering method is most suitable, wherein green forming is carried out by a metal mold forming, a CIP forming or a combination thereof, and then the green thereby obtained is fired in an inert gas atmosphere at a temperature of at least 1,400° C. To obtain a sintered body of a high density, the green forming pressure is preferably at least 2,000 kg/cm$^2$.

Now, the present invention will be described in further detail with reference to Examples and Comparative Examples.

EXAMPLE 1

20 kg of orthoboric acid (H$_3$BO$_3$), 19 kg of melamine (C$_3$N$_6$H$_6$) and 1 kg of calcium carbonate (CaCO$_3$) were mixed by a Henschel mixer, and the mixture was maintained for 6 hours under the air at a temperature of 90° C. in an atmosphere containing steam with a relative humidity of 90% by means of a thermostatic humidistat. The obtained mixture was aggregated to such an extent that when pressed gently by fingers, it was readily disintegrated. The mixture was disintegrated, whereupon by the X-ray diffractometry, it was confirmed that melamine borate (C$_3$N$_6$H$_6$.2H$_3$BO$_3$) was formed, and by the SEM photograph, the melamine borate was found to be a mixture containing particles wherein needle crystal primary particles were aggregated as shown in FIG. 2. The molar ratio (C$_3$N$_6$H$_6$.2H$_3$BO$_3$/B$_2$O$_3$) of the melamine borate to the boron oxide (B$_2$O$_3$) remaining in the unreacted H$_3$BO$_3$ residue, was 14.

The mixture containing the melamine borate particles obtained as described above, was continuously fired by means of a vertical type continuous furnace so that it passed through the heating zone at a temperature of 1,800° C. in a nitrogen atmosphere over a period of 2 hours. The sample after the firing, was pulverized to at most 150 μm and subjected to powder X-ray diffractometry, whereby it was found to be a mixture of hBN and calcium borate (3CaO.B$_2$O$_3$). The sample was mixed with a dilute nitric acid aqueous solution, followed by filtration and drying to remove the calcium borate, whereupon the SEM photograph was inspected, whereby the product was found to be a hBN powder comprising hBN particles consisting of aggregates of scaly primary particles, and other hBN particles.

Then, the product was classified into above and below 45 μm by means of a dry system vibration sieving apparatus ("Powder Tester PT-E model", manufactured by Hosokawa Micron K.K.) under such conditions that time: 1 hour, mode: VIB, and RHEOSTAT scale: 4. After the classification, the product above 45 μm was subjected to SEM observation, whereby substantially the entire amount was confirmed to be a hBN powder composed of the hBN particles of the present invention, as shown in FIG. 6. Further, the proportion of the hBN particles of the present invention constituting the hBN powder prior to the above classification, was 26 wt %.

Further, with respect to the hBN powder of the present invention obtained as described above and not subjected to classification, powder X-ray diffractometry (apparatus: "GF-2013", tradename, manufactured by Rigaku K.K.) was carried out under the conditions as identified in Table 1, whereby GI was 1.28, and OI was 16.5.

GI was calculated by the above-mentioned formula after determining the areas defined by (100), (101) and (102) diffraction lines and a linear line complemented by the base line. OI was calculated by the above-mentioned formula after determining the peak intensity ratio of the (002) and (100) diffraction lines after subtracting the background.

TABLE 1

| Target | Cu |
|---|---|
| Filter | Ni |
| Voltage | 30 kV |
| Current | 15 mA |
| High voltage | 1,350 V |
| Time constant | 2 seconds |
| Scan speed | 2°/min (2θ) |
| Divergence slit | 1° |
| Receiving slit | 0.3 mm |
| Scattering slit | 1° |
| Chart speed | 20 mm/min |

EXAMPLE 2

50 kg of H$_3$BO$_3$ and 50 kg of melamine were mixed by a ribbon blender, and the mixture was maintained for 24 hours under the air at a temperature of 80° C. in an atmosphere containing steam with a relative humidity of 80% by means of a thermostatic humidistat. The obtained mixture was aggregated to such an extent that when pressed gently with fingers, it was readily disintegrated, and from the SEM inspection, it was found to be a mixture containing particles wherein needle crystal primary particles of melamine borate were aggregated.

This mixture was continuously calcined by means of a screw conveyor furnace so that it passed through a heating zone at a temperature of 800° C. in an ammonia atmosphere over a period of 2 hours. The obtained calcined product was subjected to powder X-ray diffractometry in the same manner as in Example 1, whereby it was found to be amorphous BN. Further, the nitrogen content and the oxygen content in the calcined product were measured and found to be 49.5 wt % and 6.5 wt %, respectively. On the assumption that all of the oxygen content was $B_2O_3$, the molar ratio of $N/B_2O_3$ was obtained and found to be 26.

Then, 3 wt % of sodium carbonate ($Na_2CO_3$) was added to the calcined product, and the mixture was fired at 2,000° C. for 2 hours in a nitrogen atmosphere by means of an atmospheric gas furnace. With respect to the fired product thus obtained, powder X-ray diffractometry was carried out in the same manner as in Example 1, whereby the product was found to be hBN. The fired product was mixed with dilute nitric acid, followed by filtration and drying, whereupon the SEM photograph was inspected, whereby the product was found to be a hBN powder having the same shape as in Example 1. Further, the proportion of hBN particles above 45 μm was 40 wt %, and GI and OI were 1.41 and 9.8, respectively.

EXAMPLES 3 to 5 hBN powders were prepared under such conditions that the condition for mixing the starting materials is shown in Table 2, the condition for maintaining in the steam atmosphere is shown in Table 3, the calcining condition is shown in Table 4, and the firing condition is shown in Table 5. The obtained hBN powders were ones containing hBN particles wherein scaly primary particles were aggregated.

Comparative Examples 1 and 2

A hBN powder was prepared in the same manner as in Example 1 or Example 2 except that the mixture of boric acid and melamine was not maintained in the atmosphere containing steam. From the SEM inspection, the obtained hBN powder was found to be composed of scaly particles which were not aggregated.

Comparative Example 3

A slurry prepared by mixing 50 kg of $H_3BO_3$, 50 kg of melamine and 100 kg of water, was filtered by a filter press and then dried at a temperature of 100° C. for 48 hours in a drying oven. The obtained dried product was a bulky powder, and by the powder X-ray diffractometry, it was confirmed that melamine borate was formed. However, the results of the SEM observation was as shown in FIG. 4, i.e. the product was non-aggregated needle crystals. Using this mixture containing melamine borate, calcination, addition of the catalyst and firing were carried out in the same manner as in Example 2 to obtain a hBN powder, whereby the product was a hBN powder of a particulate form wherein scaly particles were not aggregated.

Comparative Example 4

A mixture containing melamine borate particles prepared in the same manner as in Example 5, was calcined at a temperature of 1,600° C. for 2 hours in a nitrogen atmosphere. From the powder X-ray diffractometry, the calcined product was found to be a hBN powder having a GI value of 2.8. Then, 0.5 wt % of boron oxide ($B_2O_3$) was added and mixed thereto, whereupon the nitrogen content and the oxygen content were measured, and on the assumption that all of the oxygen content was $B_2O_3$, the molar ratio of $N/B_2O_3$ was obtained and found to be 400, which was outside the scope of the present invention. This mixture was treated in the same manner as in Example 5 to obtain a hBN powder, whereby the product had a block-like particulate form.

The experimental conditions of the foregoing Examples 1 to 5 and Comparative Examples 1 to 4 are summarized in Tables 2 to 5. Their experimental results are shown in Table 6.

TABLE 2

Conditions for mixing starting materials

| | Boric acid | | Melamine amount (kg) | B/N atomic ratio | Crystallization catalyst etc. | |
|---|---|---|---|---|---|---|
| | Type | Amount (kg) | | | Type | Amount (kg) |
| Example 1 | $H_3BO_3$ | 20 | 19 | 1/2.8 | $CaCO_3$ | 1 |
| Example 2 | $H_3BO_3$ | 50 | 50 | 1/2.9 | — | — |
| Example 3 | $HBO_2$ | 30 | 55 | 1/3.8 | $2CaO \cdot B_2O_3$ | 1 |
| Example 4 | $B_2O_3$ | 60 | 100 | 1/1.4 | $Na_2CO_3$ | 3 |
| Example 5 | $H_3BO_3$ | 40 | 60 | 1/4.5 | — | — |
| Comparative Example 1 | $H_3BO_3$ | 20 | 19 | 1/2.8 | $CaCO_3$ | 1 |
| Comparative Example 2 | $H_3BO_3$ | 50 | 50 | 1/2.9 | — | — |
| Comparative Example 3 | $H_3BO_3$ | 50 | 50 | 1/2.9 | Water | 100 |
| Comparative Example 4 | $H_3BO_3$ | 40 | 60 | 1/4.5 | — | — |

TABLE 3

Conditions for maintaining in the steam atmosphere

| | Maintained or not maintained | Temp. (°C.) | Relative humidity (%) | Time (hr) | State of particles after being maintained | Molar ratio of melamine borate/$B_2O_3$ |
|---|---|---|---|---|---|---|
| Example 1 | Yes | 90 | 90 | 6 | Aggregated | 14 |
| Example 2 | Yes | 80 | 80 | 24 | Aggregated | 37 |
| Example 3 | Yes | 95 | 100 | 40 | Aggregated | 62 |
| Example 4 | Yes | 100 | 100 | 100 | Aggregated | 12 |
| Example 5 | Yes | 60 | 85 | 50 | Aggregated | 93 |
| Comparative Example 1 | No | — | — | — | — | — |

TABLE 3-continued

Conditions for maintaining in the steam atmosphere

| | Maintained or not maintained | Temp. (°C.) | Relative humidity (%) | Time (hr) | State of particles after being maintained | Molar ratio of melamine borate/$B_2O_3$ |
|---|---|---|---|---|---|---|
| Comparative Example 2 | No | — | — | — | — | — |
| Comparative Example 3 | No | — | — | — | — | — |
| Comparative Example 4 | Yes | 60 | 85 | 50 | Aggregated | 93 |

TABLE 4

| | Condition for calcination | | | | Calcined product | | Addition of catalyst | | |
|---|---|---|---|---|---|---|---|---|---|
| | | | | | Crystal phase | | | | |
| | Calcination | Temp. (°C.) | Time (hr) | Atomsphere | by X-ray diffraction | GI | Type and amount | (wt %) | Molar ratio of $N/B_2O_3$ |
| Example 1 | No | — | — | — | — | — | — | — | — |
| Example 2 | Yes | 800 | 2 | $NH_3$ | Amorphous BN | — | $Na_2CO_3$ | 3 | 26 |
| Example 3 | No | — | — | — | — | — | — | — | — |
| Example 4 | Yes | 1,600 | 2 | $N_2$ | hBN | 10.2 | $Na_2B_4O_7$ | 1 | 17 |
| Example 5 | Yes | 1,000 | 2 | $NH_3$ | Amorphous BN | — | $B_2O_3$ | 1 | 89 |
| Comparative Example 1 | No | — | — | — | — | — | — | — | — |
| Comparative Example 2 | Yes | 800 | 2 | $NH_3$ | Amorphous BN | — | $Na_2CO_3$ | 3 | 12 |
| Comparative Example 3 | Yes | 800 | 2 | $NH_3$ | Amorphous BN | — | $Na_2CO_3$ | 3 | 30 |
| Comparative Example 4 | Yes | 1,600 | 2 | $NH_3$ | hBN | 2.8 | $B_2O_3$ | 0.5 | 400 |

TABLE 5

Condition for firing

| | Temp. (°C.) | Time (hr) | Atmosphere |
|---|---|---|---|
| Example 1 | 1,800 | 2 | $N_2$ |
| Example 2 | 2,000 | 2 | $N_2$ |
| Example 3 | 1,700 | 8 | Ar |
| Example 4 | 2,100 | 1 | $N_2$ |
| Example 5 | 1,900 | 3 | $H_2$ |
| Comparative Example 1 | 1,800 | 2 | $N_2$ |
| Comparative Example 2 | 2,000 | 2 | $N_2$ |
| Comparative Example 3 | 2,000 | 2 | $N_2$ |
| Comparative Example 4 | 1,900 | 3 | $H_2$ |

TABLE 6

Experimental results

| | Crystal phase by X-ray diffraction | Form of particles | Dry classification product above 45 μm | | | |
|---|---|---|---|---|---|---|
| | | | (wt %) | Form of particles | GI | OI |
| Example 1 | hBN + $3CaO.B_2O_3$ | Aggregated particles | 26 | Aggregated particles | 1.28 | 16.5 |
| Example 2 | hBN | Aggregated particles | 40 | Aggregated particles | 1.41 | 9.8 |
| Example 3 | hBN + $3CaO.B_2O_3$ | Aggregated | 52 | Aggregated | 2.01 | 7.2 |

TABLE 6-continued

Experimental results

|  | Crystal phase by X-ray diffraction | Form of particles | Dry classification product above 45 μm (wt %) | Form of particles | GI | OI |
|---|---|---|---|---|---|---|
| Example 4 | hBN + Na$_2$B$_4$O$_7$ | Aggregated particles | 24 | Aggregated particles | 1.12 | 18.6 |
| Example 5 | hBN | Aggregated particles | 45 | Aggregated particles | 1.36 | 10.3 |
| Comparative Example 1 | hBN + 3CaO.B$_2$O$_3$ | Non-aggregated particles | 11 | Non-aggregated particles | 0.97 | 24.5 |
| Comparative Example 2 | hBN | Non-aggregated particles | 16 | Non-aggregated particles | 0.94 | 42.0 |
| Comparative Example 3 | hBN | Non-aggregated particles | 8 | Non-aggregated particles | 0.95 | 36.5 |
| Comparative Example 4 | hBN | Blocks | 36 | Blocks | 2.67 | 15.0 |

Note:
"Aggregated particles" means hBN particles wherein scaly primary particles are aggregated
"Non-aggregated particles" means non-aggregated scaly hBN particles.

EXAMPLE 6

Suitable amounts of toluene and a vulcanization agent were added to a mixture comprising 100 parts by weight of the hBN powder prior to classification, as obtained in Example 1 and 50 parts by weight of liquid silicone rubber ("CF-3110", tradename, manufactured by Toray Dow Corning Silicone K. K.), to obtain a slurry, which was formed into a green sheet by a Doctor Blade method, followed by heating and vulcanization to obtain an insulating heat radiation sheet whose thickness was 0.20 mm (0.0002 m).

This sheet was sandwiched between a copper plate and a TO-3 model heater case made of copper and set with a clamping torque of 5 kgf-cm. Then, an electric power of 15 W was applied to the heater case and maintained for 5 minutes, whereupon the temperature difference between the heater case and the copper plate was measured. The thermal resistance in the thickness direction of the insulating heat radiation sheet was calculated by thermal resistance (°C./W)=temperature difference (°C.)/electric power (W) and found to be $7.00 \times 10^{-2}$ °C./W.

Further, on the assumption that the heat conductive area of the heater case and the copper plate was 6 cm$^2$ (=0.0006 m$^2$), the thermal conductivity in the thickness direction of the insulating heat radiation sheet was calculated by thermal conductivity (W/m/°C.)=[electric power (W)×thickness of the sheet (0.0002 m)÷heat conductive area (0.0006 m$^2$)]÷temperature difference (°C.) and found to be 4.76 W/m·K.

Further, the cross-section of the obtained insulating heat radiation sheet was observed by SEM, whereby the presence of the hBN particles of the present invention was confirmed.

Comparative Examples 5 and 6

An insulating heat radiation sheet was prepared in the same manner as in Example 6 except that the hBN powder prior to classification as prepared in Comparative Example 1 or Comparative Example 4 was used (Comparative Example 5 represents the case wherein the hBN powder of Comparative Example 1 was used, and Comparative Example 6 represents the case wherein the hBN powder of Comparative Example 4 was used). As a result, the thermal conductivity of the insulating heat radiation sheet of Comparative Example 5 was 2.39 W/m·K, and that of Comparative Example 6 was 1.76 w/m·K.

Further, the cross-section of each insulating heat radiation sheet was observed by SEM, whereby in Comparative Example 5, it was confirmed that the thickness direction of scaly hBN particles is oriented to align with the thickness direction of the sheet. The hBN particles had a low thermal conductivity in the thickness direction, and it is considered that the thermal conductivity in the thickness direction of the sheet of Comparative Example 5 became lower than Example 6 because of the orientation. Further, in Comparative Example 6, no such an orientation was observed, but it is considered that the thermal conductivity became lower than Example 6, since the hBN particles of Comparative Example 4 had low crystallinity and low thermal conductivity.

EXAMPLE 7

A hBN powder having an oxygen content of 1.5 wt % and a specific surface area of 50 m$^2$/g as measured by a BET method, was mixed to the hBN powder prior to classification as prepared in Example 2 by a ribbon blender to obtain a starting material powder for producing a hBN sintered body having an oxygen content of 1.0 wt %. This powder was subjected to hot press sintering under a surface pressure of 150 kg/cm$^2$ at a temperature of 1,900° C. for one hour to obtain a hBN sintered body. With respect to the obtained hBN sintered body, the density, the three-point bending strength and the BN purity were measured, and at the same time, the surface which was in parallel with the pressing direction, was subjected to machining, whereupon the presence or absence of chipping on the processed surface, was inspected. The results are shown in Table 7.

Comparative Example 7

A hBN sintered body was prepared and evaluated in the same manner as in Example 7 except that the hBN powder before classification as prepared in Comparative Example 2, was used. The results are shown in Table 7.

TABLE 7

|  | Density (g/cm$^3$) | Three-point bending strength (MPa) | BN purity (wt %) | Presence or absence of chipping |
|---|---|---|---|---|
| Example 7 | 1.90 | 45 | 99.6 | Absence |
| Comparative Example 7 | 1.80 | 25 | 99.5 | Presence |

Comparative Example 8

Hot press sintering was carried out in the same manner as in Example 7 except that the oxygen content of the starting material powder for producing a hBN sintered body was changed to 0.3 wt %, whereby sintering did not proceed.

EXAMPLE 8

90 Parts by weight of the hBN powder prior to classification as obtained in Example 2, 0.8 part by weight of calcium oxide and 9.2 parts by weight of boron oxide were mixed by a ribbon blender to obtain a starting material powder for preparing a pressureless sintered body of hBN. This powder was formed with metal mold under a surface pressure of 200 kg/cm$^2$ and then subjected to CIP forming under a surface pressure of 2,700 kg/cm$^2$, and the formed product was subjected to pressureless sintering at a temperature of 1,600° C. for 1 hour in an argon gas atmosphere. The obtained pressureless sintered body had a density of 1.96 g/cm$^3$ and a three-point bending strength of 75 MPa.

Comparative Example 9

A pressureless sintered body of hBN was prepared in the same manner as in Example 8 except that the hBN powder before classification as obtained in Comparative Example 2, was used. This sintered body had a density of 1.75 g/cm$^3$ and a three-point bending strength of 43 MPa.

As described in the foregoing, by the melamine borate particles of the present invention, it is possible to produce hBN particles in which scaly primary particles are aggregated, or a hBN powder containing such hBN particles.

By the hBN particles or the hBN powder containing such hBN particles of the present invention, it is possible to produce a resin or rubber product, or a hBN sintered body, having small anisotropy without impairing the excellent properties of hBN.

According to the method for producing a hBN powder of the present invention, it is possible to produce a hBN powder having the above-mentioned properties in good yield and at a low cost.

By the starting material powder for producing a hBN sintered body or the hBN sintered body of the present invention, it is possible to obtain a hBN sintered body of a high purity and high density excellent in mechanical properties, or a pressureless sintered body of hBN of a high density and high strength with small anisotropy.

We claim:

1. Hexagonal system boron nitride particles each consisting essentially of scaly primary particles of hexagonal system boron nitride which are aggregated to one another without orientation.

2. The hexagonal system boron nitride particles according to claim 1 wherein the primary particles are aggregated to one another in a pinecone form without a binder.

3. A hexagonal system boron nitride powder, which is a mixture comprising from 20 to 100 wt % of hexagonal system boron nitride particles as defined in claim 1 or 2 and from 80 to 0 wt % of other boron nitride particles, and which has a graphitization index (GI) of from 1.0 to 2.5 by powder X-ray diffractometry and a ratio of $I_{002}/I_{100}$ of from 6 to 20, where $I_{002}$ is the intensity of the (002) diffraction line and $I_{100}$ is the intensity of the (100) diffraction line.

4. A composite comprising a resin and/or rubber, and a hexagonal system boron nitride powder as defined in claim 3, incorporated thereto.

5. A powder material for preparation of a sintered body of hexagonal system boron nitride, which contains a hexagonal system boron nitride powder as defined in claim 3 and has an oxygen content of from 0.5 to 2.5 wt %.

6. A hexagonal system boron nitride powder material for preparation of a pressureless sintered body, which comprises a hexagonal system boron nitride powder as defined in claim 3, and at least one member selected from the group consisting of boron oxides, alkaline earth metal oxides and alkaline earth metal borates, incorporated to the powder in an amount of from 1 to 20 wt %.

* * * * *